(12) United States Patent
Mehta et al.

(10) Patent No.: US 11,957,681 B2
(45) Date of Patent: Apr. 16, 2024

(54) LIQUID DOSAGE FORMS OF IMATINIB

(71) Applicant: SHORLA PHARMA LTD., County Tipperary (IE)

(72) Inventors: Sandip Mehta, Ahmedabad (IN); Vijay Patel, Ahmedabad (IN); Manish Umrethia, Ahmedabad (IN); Jayanta Kumar Mandal, Ahmedabad (IN)

(73) Assignee: SHORLA PHARMA LIMITED, County Tipperary (IE)

( * ) Notice: Subject to any disclaimer, the term of this patent is extended or adjusted under 35 U.S.C. 154(b) by 641 days.

(21) Appl. No.: 16/634,475

(22) PCT Filed: Jul. 26, 2018

(86) PCT No.: PCT/IB2018/055583
§ 371 (c)(1),
(2) Date: Jan. 27, 2020

(87) PCT Pub. No.: WO2019/021229
PCT Pub. Date: Jan. 31, 2019

(65) Prior Publication Data
US 2022/0160709 A1      May 26, 2022

(51) Int. Cl.
| | | |
|---|---|---|
| A61K 31/506 | (2006.01) | |
| A61K 9/00 | (2006.01) | |
| A61K 9/08 | (2006.01) | |
| A61K 9/10 | (2006.01) | |
| A61K 47/02 | (2006.01) | |
| A61K 47/10 | (2017.01) | |
| A61K 47/12 | (2006.01) | |
| A61K 47/14 | (2017.01) | |
| A61K 47/26 | (2006.01) | |
| A61K 47/34 | (2017.01) | |

(52) U.S. Cl.
CPC .......... *A61K 31/506* (2013.01); *A61K 9/0053* (2013.01); *A61K 9/08* (2013.01); *A61K 9/10* (2013.01); *A61K 47/02* (2013.01); *A61K 47/10* (2013.01); *A61K 47/12* (2013.01); *A61K 47/14* (2013.01); *A61K 47/26* (2013.01); *A61K 47/34* (2013.01)

(58) Field of Classification Search
None
See application file for complete search history.

(56) References Cited

FOREIGN PATENT DOCUMENTS

WO    WO 2014/041551    *   3/2014   ............. A61K 47/10

* cited by examiner

*Primary Examiner* — Craig D Ricci
(74) *Attorney, Agent, or Firm* — Harness, Dickey & Pierce, P.L.C.

(57) ABSTRACT

Imatinib is approved and marketed in solid oral dosage forms which may be dispersed in water or apple juice for patients having swallowing difficulty. Dispersion of Imatinib solid dosage forms in apple juice may increase palatability and patient compliance but apple juice may not be available all the time for administration. Further, dispersion of Imatinib solid oral dosage forms may not administer correct and consistent dose of medicine every time. The present invention therefore provides liquid dosage forms of Imatinib which correctly and consistently administers correct dose of drug to the patients.

1 Claim, No Drawings

LIQUID DOSAGE FORMS OF IMATINIB

CLAIM OF PRIORITY

This application is a U.S. national stage filing under 35 U.S.C. § 371 of International Application No. PCT/IB2018/055583 filed Jul. 26, 2018, entitled "LIQUID DOSAGE FORMS OF IMATINIB", which in turn claims priority to Indian Application No. 201721026519 filed Jul. 26, 2017, and Indian Application No. 201823010403 filed on Mar. 21, 2018, each of which is incorporated herein by reference in its entirety.

FIELD OF THE INVENTION

The present invention relates, in general, to the pharmaceutical field, and more precisely it relates to the liquid dosage forms of protein-tyrosine kinase inhibitor such as Imatinib or pharmaceutically acceptable salt thereof. In particular, the present invention relates to ready to use, liquid dosage forms of Imatinib or pharmaceutically acceptable salt thereof and to the processes for the preparation thereof.

BACKGROUND OF THE INVENTION

Imatinib, chemically known as N-(4-methyl-3-{[4-(pyridin-3-yl)pyrimidin-2-yl]amino}phenyl)-4-[(4-methylpiperazin-1-yl)methyl]benzamide having an empirical formula $C_{29}H_{31}N_7O$ and a molecular weight of 493.6 gm/mol has a following structural formula:

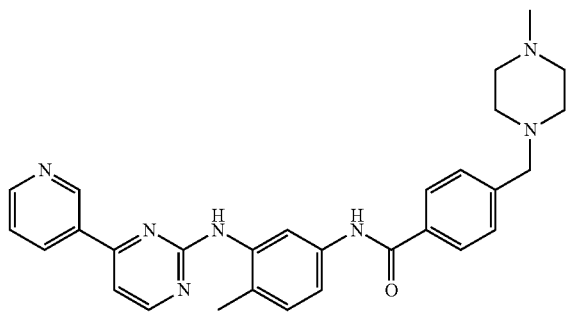 [SMILES: Cc1ccc(NC(=O)c2ccc(CN3CCN(C)CC3)cc2)cc1Nc1nccc(-c2cccnc2)n1]

Imatinib mesylate is a protein-tyrosine kinase inhibitor; it inhibits the abnormal functioning Bcr-Abl tyrosine kinase, which is produced by the Philadelphia chromosome abnormality, found in chronic myeloid leukemia (CML). Imatinib inhibits cell proliferation and induces apoptosis (programmed cell death) in the Bcr-Abl cell lines and in the leukemic cells generated by CML. Imatinib also inhibits proliferation and induces apoptosis in gastrointestinal stromal tumor (GIST) cells, which express an activating c-kit mutation. More recently, the drug has been approved for the treatment of mesenchymal cell neoplasms of the intestinal tract.

It has now been discovered that Imatinib mesylate can be used as a treatment for patients suffering from hepatic fibrosis based on its ability to downregulate stellate cell activation in culture and in vivo.

Imatinib mesylate is well absorbed after oral administration with Cmax achieved within 2-4 hours post-dose. It was also reported that mean absolute bioavailability is 98%. Biotransformation of Imatinib mesylate is via hepatic metabolism and cytochrome P450 enzymes (especially CYP3A4). Imatinib mesylate is converted to its main circulating active metabolite, a N-desmethylated piperazine derivative. This derivative, in vitro, has potency similar to Imatinib mesylate and comprises about 15% of the AUC (area under the curve) for Imatinib mesylate. When imatinib mesylate is orally administered, the elimination half-lives of Imatinib mesylate and its major active metabolite, the N-desmethyl derivative, are approximately 18 and 40 hours, respectively and the time to reach peak concentration is 2 to 4 hours.

Imatinib mesylate is presently available as tablet form of 100 mg and 400 mg. The approved dosage range for imatinib mesylate in the treatment of CML is 400 mg to 800 mg (400 mg twice a day) and 600 mg per day for gastrointestinal stromal tumors (GIST).

It was reported that amounts of imatinib mesylate effective to treat hepatic fibrosis would broadly range between about 50 mg and about 600 mg per day and preferably between about 50 mg and about 200 mg per day administered orally.

Prior art reveals that Imatinib or pharmaceutically acceptable salt thereof has been formulated into solid dosage forms. Liquid dosage forms of Imatinib or pharmaceutically acceptable salt thereof are not much explored by the formulation scientists. The prior arts mentioned in the forthcoming paragraphs are incorporated herein by references for all the purposes.

EP 1895984 and US 20060275372 describes a stable nanoparticulate composition of imatinib mesylate, or a salt thereof and at least one surface stabilizer. EP 2009008 discloses a pharmaceutical composition comprising imatinib mesylate having less than about 0.09% area HPLC percent units of desmethyl-imatinib mesylate and at least one pharmaceutically acceptable excipients. EP 2120877 and US 2010087444 describes a solid dispersion of imatinib mesylate comprising imatinib mesylate and a pharmaceutically acceptable carrier, wherein said carrier is a cellulose derivative.

US 2016143850 and EP 3019159 describes a granulate composition of imatinib mesylate comprising of imatinib mesylate, binder and of disintegrant.

US 2008119479 discloses a pharmaceutical composition which comprises ZD6474 or a pharmaceutically acceptable salt thereof, and imatinib, in association with a pharmaceutically acceptable excipient or carrier. EP 2782560 and US 2015125534 discloses a pharmaceutical powder formulation comprising granules of a tyrosine kinase inhibitor, wherein the granules of the tyrosine kinase inhibitor are coated with an enteric coating, wherein the tyrosine kinase inhibitor is present in an amount of up to 23% by weight based on the total weight of the pharmaceutical powder formulation.

WO 2006132930 discloses a pharmaceutical combination comprising a pyrimidylaminobenzamide compound and Imatinib.

U.S. Pat. Nos. 8,653,093, 7,767,688, EP 1893213 and WO 2006132930 discloses a medicament for the treatment of gastrointestinal stromal tumours by use of a pharmaceutical combination comprising of 4-Methyl-3-[[4-(3-pyridinyl)-2-pyrimidinyl]amino]-N-[5-(4-methyl-1H-imidazol-1-yl)-3-(trifluoromethyl)phenyl] benzamide or a pharmaceutically acceptable salt thereof, and imatinib or a pharmaceutically acceptable salt thereof.

WO 2014041551 (hereinafter referred as '551 publication) discloses oral aqueous solution comprising Imatinib or pharmaceutically acceptable acid addition salts or polymorphs thereof, process for preparing such solution and their use in the treatment of chronic myeloid leukemia, gastrointestinal stromal tumors. The specification of '551 publication teaches oral aqueous solution which essentially comprises viscosity regulating agent that is used to stabilize the active ingredient (i.e. Imatinib mesylate) or increase the viscosity of the oral solution. Preferred viscosity regulating agents according to the specification of '551 publication are polyvinyl pyrrolidone and hypromellose. Such preferred viscosity regulating agent has not been used in the oral solutions of the present invention being the first major difference between the present invention and the invention disclosed in the specification of '551 publication. Thus, the stability achieved by the oral solution of the present invention and results provided in the present specification are without using (i) viscosity regulating agents preferred in the specification of '551 publication, and (ii) any additional stabilizing agent.

Further, the specification of '551 publication does not provide stability results of the oral solution prepared therein. Upon reading the specification of '551 publication, a skilled person cannot have an idea regarding stability and shelf life of the Imatinib oral solution disclosed therein. What the specification provides is mere statement that "the formulation is found to be stable throughout the period of the stability study." (See page 19; lines 13-14) The specification of '551 does not define what should be considered as "stable" and also that what is the period of "stability study". Therefore it is difficult for a skilled person to envisage stability of the oral solution disclosed in the specification of '551 publication.

Another major difference between the invention disclosed in the specification of '551 publication and the present invention is that the oral solution of Imatinib disclosed in the specification of '551 publication is shown supra-bioavailable (which means the AUC and Cmax of the oral solution disclosed in the specification of '551 publication is higher than either the acceptable values or values shown by Imatinib tablets) when tested in rats against Imatinib tablets, whereas the oral solution of the present invention has been found bioequivalent (which means all the pharmacokinetic parameters such as AUC, Cmax is within the acceptable limits when compared with Imatinib tablets) to the marketed Gleevec (Imatinib) tablets during clinical studies in humans. Further, supra-bioavailability may not be advantageous as sometimes it may lead to toxicity and/or other side effects. Furthermore, just because the oral solution disclosed in the specification of '551 publication is supra-bioavailable in rats does not necessarily mean that it can be administered to humans. Thus, the oral solution of Imatinib according to the present invention is ready to use for human administration.

Currently available preparations of Imatinib are solid oral preparations e.g. tablets, and capsules. These preparations have their own disadvantages and limitations, for example they are not suitable for all types of patient populations. Therefore there is an existing need for liquid dosage forms of Imatinib having prolonged stability and palatability.

Compared to the conventional tablets and capsules, oral liquid dosage forms including solutions, syrups, suspensions, elixirs, and concentrates offer unique advantages to many patients. For example, liquids may provide better patient compliance for those with swallowing difficulties and better dosage control versus a fixed tablet dose. Hence, liquid dosage forms are generally formulated for use in geriatric and pediatric patients. However, there are also a number of "challenges" surrounding the formulation and development of these forms.

Children generally reject taking medicine which does not have a favorable shape, taste, flavor, etc. However, if a child who needs to take a medicine, rejects taking it, he might never recover from his condition. When a child is unable to take medicine orally, it is intravenously administered, and he and his caregivers then may experience stress. Syrups and suspensions are considered as favorable types of dosage forms in which to orally administer medicine to infants and children.

However, they may have disadvantages such as solubility, a bad taste, portability problems or required refrigerator storage. Palatability is one of the main elements of patient acceptability of an oral pediatric medicine. Palatability is defined as the overall appreciation of an oral medicinal product in relation to its smell, taste, aftertaste and feeling in the mouth. Design of the formulation of an oral pediatric medicine should be considered together with its palatability.

According to Gleevec® prescribing information, Gleevec® tablets can be dissolved in water or apple juice for patients having swallowing difficulty but in any treatment an important consideration is to ensure that the patient receives the correct dose of medicine. Administration of Gleevec® tablets by dissolving in water or apple juice may not administer correct and consistent dose every time. Disadvantages associated with such an administration is that (i) Gleevec tablets take much longer time to get dispersed in water or apple juice and (ii) it leaves behind lots of residues in the container after administration resulting into the administration of incorrect dose. Further, Imatinib has bitter taste and administration with apple juice may mask its taste and increase the palatability and patient compliance. But apple juice or any other flavored beverage may not be available all the time while administering a drug to the patient. It may therefore happen that patients have to take medicines with water which creates cloying sensation in their mouth. It will therefore be desirable to have Imatinib containing dosages in liquid forms which also contain sweeteners and flavors which makes such dosage forms palatable and more patient compliant. Further, liquid dosage forms provide assurance of dosage uniformity upon administration to patients and eliminates difficulty of administration. Liquid dosage forms can also provide physicians more flexibility in designing dosage regimens for patients. Such liquid dosage forms are advantageous to pediatric patients, geriatric patients and those patients who are unable to take oral therapy.

OBJECTS OF THE INVENTION

Because of their liquid character, liquid dosage forms represent an ideal dosage form for patients who have difficulty swallowing tablets or capsules. This factor is of particular importance in administration of drugs to children and aged patients. Further, as mentioned above, administration of Imatinib tablets by dispersing in water or apple juice is also not preferred because of administration of incorrect and inconsistent dose every time. It is therefore principal object of the present invention to provide liquid dosage forms of Imatinib or pharmaceutically acceptable salt thereof. The liquid dosage forms of the present invention are useful for administering to pediatric, geriatric patients and other patients who are unable to take solid oral therapy. The liquid dosage forms according to the present invention include liquids, liquid dispersions, suspensions, solutions, emulsions, sprays, spot-on, syrups, elixirs, drops, gels, solution-gels, concentrates and the like.

Liquid dosage forms are designed as ready to use liquids and as powder for reconstitution into liquid orals like syrups, solutions, suspensions and emulsions. Powder for reconstitution may require skills & expertise and needs to be prepared by a healthcare provider and may not be prepared by the patient or caregiver. The reconstitution process may also be a time consuming process and the patient cannot be benefited by the immediate dose of Imatinib as and when required. In such a situation, ready to use, liquid dosage forms of Imatinib may be very useful and the patients can be given required doses immediately using ready to use, liquid dosage forms of Imatinib. Therefore, a yet another object of the present invention is to provide ready to use, liquid dosage forms of Imatinib or pharmaceutically acceptable salt thereof.

The solution dosage form can be a viable alternative for patients who have problems in swallowing the tablet or capsule dosage form. It provides assurance of dosage uniformity upon administration to patients and eliminates difficulty of administration. A solution can also provide physicians more flexibility in designing dosage regimens for patients. Imatinib solution dosage form is suitable for administration to both pediatric and geriatric patients while also compensating for a good organoleptic properties and remaining suitably stable. Hence, the development of a liquid formulation is therefore desirable since it offers improved patient compliance. A yet another object of the present invention is therefore to develop solution dosage forms of Imatinib or pharmaceutically acceptable salt thereof. The solution dosage forms according to the present invention comprises Imatinib or pharmaceutically acceptable salt thereof and one or more pharmaceutically acceptable excipients or additives selected from the group comprising of vehicles, solvents/co-solvents, solubilizers, surfactants, pH adjusting agents and/or pH modifying agents and/or buffering agents or any combination thereof. The solution dosage forms according to the present invention may further comprise one or more agents selected from the group comprising of preservatives, sweetening agents, flavoring agents and coloring agents or any combination thereof.

Suspensions possess certain advantages over other liquid dosage forms. Some drugs are insoluble in all acceptable media and must, therefore, be administered as a tablet, capsule, or as a suspension. In addition, disagreeable tastes can be masked by a suspension of the drug or a derivative of the drug. Drugs in suspension are chemically more stable than in solution. In another object, the present invention therefore provides suspension dosage forms of Imatinib or pharmaceutically acceptable salt thereof. The suspension dosage forms according to the present invention comprises Imatinib or pharmaceutically acceptable salt thereof and one or more pharmaceutically acceptable excipients or additives selected from the group comprising of vehicles, solvents/co-solvents, solubilizers, suspending agents/thickening agents/viscosity modifying agents, anti-foaming agents, anti-caking agents, wetting agents, surfactants, pH adjusting agents and/or pH modifying agents and/or buffering agents or any combination thereof. The suspension dosage forms according to the present invention may further comprise one or more agents selected from the group comprising of preservatives, sweetening agents, flavoring agents and coloring agents or any combination thereof.

A yet another object of the present invention is to provide liquid dosage forms of Imatinib or pharmaceutically acceptable salt thereof having palatability, prolonged stability and improved and/or comparable pharmacokinetic profile or bioavailability when compared to the known or marketed Imatinib formulations. The liquid dosage forms of the present invention comprise sweetener(s) and flavoring agent(s) which masks the bitter taste of Imatinib and provides pleasant taste.

A yet another object of the present invention is to provide process for the preparation of liquid dosage forms of Imatinib or pharmaceutically acceptable salt thereof.

A yet another object of the present invention is to provide use of the liquid dosage forms of the present invention in the manufacture of a medicament.

A yet another object of the present invention is to provide liquid dosage forms of the present invention for use as a medicament.

A yet another object of the present invention is to provide method for the treatment of a disease or disorder that can be treated by inhibiting protein-tyrosine kinase comprising administering to a patient, such as human, an effective dosage amount of a liquid dosage form comprising Imatinib or pharmaceutically acceptable salt thereof and one or more pharmaceutically acceptable excipients or additives as disclosed and described herein. A yet another object of the present invention is to provide method for the treatment of a tumor disease or cancer disease comprising administering to a patient, such as human, an effective dosage amount of a liquid dosage form comprising Imatinib or pharmaceutically acceptable salt thereof and one or more pharmaceutically acceptable excipients or additives as disclosed and described herein. A yet another object of the present invention is to provide method for the treatment of at least one disease or condition selected from the group comprising of chronic myeloid leukemia, acute lymphoblastic leukemia, myelodysplastic diseases, myeloproliferative diseases, aggressive systemic mastocytosis, hypereosinophilic syndrome and/or chronic eosinophilic leukemia, unresectable, recurrent and/or metastatic dermatofibrosarcoma protuberans, and unresectable and/or metastatic malignant gastrointestinal stromal tumors comprising administering to a patient, such as human, an effective dosage amount of a liquid dosage form comprising Imatinib or pharmaceutically acceptable salt thereof and one or more pharmaceutically acceptable excipients or additives as disclosed and described herein.

A yet another object of the present invention is to use the liquid dosage forms of the present invention for the treatment of a disease or disorder that can be treated by inhibiting protein-tyrosine kinase. A yet another object of the present invention is to use the liquid dosage forms of the present invention for the treatment of a tumor disease or a cancer disease. A yet another object of the present invention is to use the liquid dosage forms of the present invention for the treatment of at least one diseases or condition selected from the group comprising of chronic myeloid leukemia, acute lymphoblastic leukemia, myelodysplastic diseases, myeloproliferative diseases, aggressive systemic mastocytosis, hypereosinophilic syndrome and/or chronic eosinophilic leukemia, unresectable, recurrent and/or metastatic dermatofibrosarcoma protuberans, and unresectable and/or metastatic malignant gastrointestinal stromal tumors.

DETAILED DESCRIPTION OF THE INVENTION

Characteristics of an active drug are of major concern in developing an oral liquid dosage formulation. The major challenges in developing oral liquid dosage forms are (i) the stability of a drug in aqueous solution, suspension or emulsion, (ii) the solubility of a drug at the required level, and (iii) an acceptable taste and (iv) to be bioavailable when taken orally. It is the effective use of excipients, which allows formulators overcome these challenges. Additionally, an excipient's compatibility with a drug in the solid state cannot infer the same compatibility in liquid dosage.

The decision to develop a solution, syrup or a suspension of a drug is influenced by many factors like solubility, particle size and the desired release profile of the drug and properties of the base vehicle like surface tension, viscosity, boiling point, and specific heat of solution, all of which may be affected in various ways. In case of clear liquids, lack of solubility of the drug in the base vehicle may demand the need for miscible pharmaceutical co-solvents. Similarly, a miscible solvent may be needed to decrease the solubility of the drug in a primary vehicle in formulating a suspension.

The therapeutic utility of drugs involves the application of dosage forms/delivery systems, which serve as carrier systems together with several excipients to deliver the active therapeutic agent to the site of action. Suspensions are an important class of pharmaceutical dosage forms that may be given by many routes, including oral, topical, parenteral, and also used in the eye for ophthalmic purposes. Surprisingly, large proportions of new drug candidates that are emerging are predominantly water insoluble and, therefore, demonstrate poor bioavailability in the solution dosage form. While suspensions present a viable formulation option for many drugs, particularly for water insoluble, hydrophobic drug substances, there are certain criteria that a well-formulated suspension should meet.

The suspension dosage form has long been used for poorly soluble active ingredients for various therapeutic indications. Development of stable suspensions over the shelf life of the drug product continues to be a challenge on many fronts. Drugs from suspension formulations typically exhibit an improved bioavailability when compared to the same drug formulated as a tablet or capsule.

A good understanding of the fundamentals of disperse systems is essential in the development of a suitable pharmaceutical suspension. The development of a suspension dosage form follows a very complicated path. The selection of the proper excipients (surfactants, viscosity imparting agents etc.) is important. The particle size distribution in the finished drug product dosage form is a critical parameter that significantly impacts the bioavailability and pharmacokinetics of the product.

The advantages of suspension dosage forms include effective dispensing of hydrophobic drugs; avoidance of the use of co-solvents; masking of unpleasant taste of certain ingredients; offering resistance to degradation of drugs due to hydrolysis, oxidation or microbial activity; easy swallowing for young or elderly patients; and efficient intramuscular depot therapy. In addition, when compared to solution dosage forms, relatively higher concentration of drugs can be incorporated into suspension products. To date, numerous theories have been introduced and successfully used to explain the unique behavior of suspension preparations.

An important consideration in any treatment regime is to ensure that the patient receives the correct dose of medicine. For many patients and many drugs there is an acceptable dose window that allows fixed-dose medicines to be used to treat patients with a wide range of body weights without the need to precisely adjust the dose.

However, there are other groups of patients where the "fixed-unit-dose" model may not be appropriate, depending on the drug's therapeutic index and pharmacokinetics, e.g. pediatric patients, geriatric patients, patients with severe renal insufficiency and patients with severe hepatic insufficiency. Oral solid unit dose forms, e.g. tablets and capsules, are not convenient under such circumstances since they are fixed strength unit dose forms. In contrast, oral liquid dose forms do have the in-built flexibility that allows the dose to be tailored to the patients' needs.

Where the drug is sufficiently soluble, a solution dosage form, e.g. a simple mixture, may be used. But not all drugs are sufficiently soluble to allow suitable strength solution medicines to be developed and manufactured with an acceptable shelf-life. In such cases, an alternative approach could be to develop a stable aqueous suspension that will allow consistent dosing of the patient. Pharmaceutical suspensions have several advantages and disadvantages when compared to other dosage forms. Since suspensions are liquids, dose adjustment for patients with renal or hepatic impairment, or for pediatric or geriatric patients, may be more straightforward. This is an oversimplification of the development of a dosing strategy for a drug candidate. There are many other details that must be considered for a formulation development project to be successful, but it does provide a simple overview of some of the issues.

The suspension must be physically stable (no appreciable settling) for a sufficient time, chemically stable over the required time (shelf-life), possess a viscosity that allows it to be used for its intended purpose, be easily reconstituted by shaking, and be acceptable in use to the patient, care-giver or other user.

Some materials may possess a combination of properties useful in the formulation and manufacture of stable, elegant pharmaceutical suspensions. Formulation scientists need to consider the totality of properties possessed by a particular excipient. Even though it is being added for one particular characteristic, the other properties will still be present, and will still influence the formulation.

Many of the recently discovered active pharmaceutical ingredients are quite hydrophobic with limited solubility. They may also be quite distasteful. Other drugs may also have quite a high chemical degradation precluding them to be administered as aqueous solutions, and in this case, it may be possible to synthesize an insoluble derivative. In other cases, some drugs are required to be present in the gastrointestinal tract or in the pre-corneal pocket with long residence time. For such drugs, a suspension is an ideal delivery system as it provides better chemical stability and larger surface area and is often more bioavailable than aqueous solutions, tablets, and capsules.

Formulation of an elegant, stable, preserved, safe, and effective suspension is a technically challenging task compared aqueous solutions, tablets, and capsules. Pharmaceutical suspensions are thermodynamically unstable systems. Thus, preparation of such systems is often associated with problems of physical stability, content uniformity, sedimentation, caking, re-suspendibility, and crystal growth. Furthermore, issues related to the masking of bitter taste and undesirable odor of the pharmaceutical ingredient must be taken into consideration.

Some desirable attributes of a suspension are described as follows,

1. It should be safe, effective, stable, and pharmaceutically elegant during the shelf life of the product.

2. The drug should not have a quick sedimentation rate. Furthermore, it should re-suspend easily upon shaking and it must not cake.

3. Physical attributes such as particle size, particle size distribution, viscosity should remain fairly uniform throughout the shelf life of the product.

4. Its viscosity must promote free and uniform flow from the container. The product must be appropriately substantive that it spreads freely over the affected area.

5. Re-suspension should produce a homogeneous mix of drug particles such that there is a content uniformity with each dose.

A quick means to identify whether or not a drug may be more suitable for solution or suspension is to overlap the pH-stability profile with the pH-solubility profile. This overlap creates a window, which may suggest which dosage form might be most desirable and subsequently the type of excipients needed.

Oral liquid formulation needs a meticulous blend of ingredients to perform various functions like wetting and solubilization, stabilization and to impart suitable color, taste and viscosity. The blend should be compatible, non-reactive and stable. The common excipients generally required for any liquid formulation are vehicles (base), viscosity builders, stabilizers, preservatives, colors and flavors. In addition, solubilizers are required in case of clear liquids, suspending agents are needed for suspensions and emulsifying agents for emulsions.

Imatinib is an inhibitor of protein-tyrosine kinase and commercially available as tablets (Gleevec®) in the United States since 2003 and is indicated for the treatment of chronic myelogenous leukemia (CML) and acute lymphocytic leukemia (ALL) that are Philadelphia chromosome-positive (Ph+) and certain types of gastrointestinal stromal tumors (GIST), systemic mastocytosis, and myelodysplastic syndrome. According to Gleevec® prescribing information, Gleevec® tablets can be dissolved in water or apple juice for patients having swallowing difficulty but in any treatment an important consideration is to ensure that the patient receives the correct dose of medicine. Administration of Gleevec® tablets by dissolving in water or apple juice may not administer correct and consistent dose every time. In the principal aspects, the present invention therefore provides liquid dosage forms of Imatinib or pharmaceutically acceptable salt thereof.

The liquid dosage forms according to the present invention include, but not limited to, liquids, liquid dispersions, suspensions, solutions, emulsions, ointments, creams, sprays, spot-on, syrups, elixirs, drops, gels, solution-gels, concentrates and the like.

Such liquid dosage forms can be prepared using appropriate one or more pharmaceutically acceptable excipients or additives. Such excipients or additives may be known to those skilled in the art.

The solution dosage form can be a viable alternative for patients who have problems in swallowing the tablet or capsule dosage form. It provides assurance of dosage uniformity upon administration to patients and eliminates difficulty of administration.

A solution can also provide physicians more flexibility in designing dosage regimens for patients. Imatinib solution dosage form is suitable for administration to both pediatric and geriatric patients while also compensating for a good organoleptic properties and remaining suitably stable. Hence, the development of a liquid formulation is therefore desirable since it offers improved patient compliance. In one of the further aspects, the present invention therefore provides solution dosage forms of Imatinib or pharmaceutically acceptable salt thereof.

Suspensions possess certain advantages over other liquid dosage forms. Some drugs are insoluble in all acceptable media and must, therefore, be administered as a tablet, capsule, or as a suspension. In addition, disagreeable tastes can be masked by a suspension of the drug or a derivative of the drug. Drugs in suspension are chemically more stable than in solution. Therefore, in one of the further aspects, the present invention provides suspension dosage forms of Imatinib or pharmaceutically acceptable salt thereof.

Liquid dosage forms are designed as ready to use liquids and as powder for reconstitution into liquid orals like syrups, solutions, suspensions and emulsions. Powder for reconstitution may require skills & expertise and needs to be prepared by a healthcare provider and may not be prepared by the patient or caregiver. The reconstitution process may also be a time consuming process and the patient cannot be benefited by the immediate dose of Imatinib as and when required. In such a situation, ready to use, liquid dosage forms of Imatinib may be very useful and the patients can be given required doses immediately using ready to use, liquid dosage forms of Imatinib. In one of the further aspects, the present invention therefore provides ready to use, liquid dosage forms of Imatinib or pharmaceutically acceptable salt thereof.

Liquid dosage forms of an active drug can be prepared using one or more pharmaceutically acceptable excipients or additives suitable for the preparation of liquid dosage forms. In one of the further aspects, the present invention provides liquid dosage forms of Imatinib or pharmaceutically acceptable salt thereof and one or more excipients or additives suitable for preparing liquid dosage forms.

The term "pharmaceutically acceptable excipients or additives" as used herein refers to such pharmaceutically acceptable excipients which are known to those skilled in the art for the purposes of preparing liquid dosage forms of the present invention. Such pharmaceutically acceptable excipients, without limitation include, vehicles, solvents/co-solvents, solubilizers, solubility enhancing agents, tonicity agents, permeation/penetration enhancers, mucoadhesives, suspending agents/thickening agents/viscosity modifying agents, bulking agents/auxiliary suspending agents, wetting agents, anti-foaming agents, anti-caking agents, stabilizing agents, anti-oxidants, chelating agents, buffering agents/pH modifying agents/pH adjusting agents, surfactants, preservatives, sweetening agents, flavouring agents and the like or any combination thereof. Such pharmaceutically acceptable excipients can be used in an amount which provides the liquid dosage forms of the present invention desired property for which they are intended or desired to use.

In one of the further aspects, the present invention provides liquid dosage forms of Imatinib in the form of solution dosage forms comprising Imatinib or pharmaceutically acceptable salt thereof and one or more pharmaceutically acceptable excipients or additives selected from the group comprising of vehicles, solvents/co-solvents and/or solubilizers, pH adjusting agents and/or pH modifying agents and/or buffering agents or any combination thereof. One or more surfactants may also be added in the solution dosage forms of the present invention.

In one of the further aspects, the present invention provides liquid dosage forms of Imatinib in the form of suspension dosage forms comprising Imatinib or pharmaceutically acceptable salt thereof and one or more pharmaceutically acceptable excipients or additives selected from the group comprising of vehicles, solvents/co-solvents and/or solubilizers, suspending agents/thickening agents/viscosity modifying agents, anti-foaming agents, surfactants, antioxidants, pH adjusting agents and/or pH modifying agents and/or buffering agents or any combination thereof. One or more anti-caking agents may also be added in the suspension dosage forms of the present invention.

Microbiological contamination presents a significant health hazard in oral liquids. Therefore, the use of preservatives become inevitable to prevent the growth of microorganisms during the product's manufacture and shelf life. Therefore, in one of the further aspects, the liquid dosage forms of the present invention may also comprise antimicrobial agents or preserving agents or preservatives.

Increase in the palatability of the drug formulations increases the patient compliance and patient acceptability towards the drug. In one of the further aspects, the present invention therefore provides palatable liquid dosage forms comprising Imatinib or pharmaceutically acceptable salt thereof and at least one or both selected from sweeteners/sweetening agents and flavouring agents.

The liquid dosage forms according to the present invention, without limitation include, aqueous dosage forms, alcoholic and/or hydro-alcoholic dosage forms and non-aqueous dosage forms. Aqueous dosage forms according to the present invention may also comprise one or more non-aqueous and/or organic solvents.

In certain aspects, the present invention provides liquid dosage forms of Imatinib in the form of suspensions comprising Imatinib or pharmaceutically acceptable salt thereof, vehicle(s), solvent(s)/co-solvent(s), solubilizer(s), suspending agent(s)/thickening agent(s)/viscosity modifying agent (s), preservative(s), anti-foaming agent(s), wetting agent(s), surfactant(s), pH adjusting agent(s)/pH modifier(s) or buffering agent(s) or both, sweetener(s) and flavoring agent(s).

In certain aspects, the present invention provides liquid dosage forms of Imatinib in the form of solutions comprising Imatinib or pharmaceutically acceptable salt thereof, vehicle(s), solvent(s)/co-solvent(s), solubilizer(s), preservative(s), surfactant(s), pH adjusting agent(s)/pH modifier(s) or buffering agent(s) or both, sweetener(s) and flavoring agent(s).

In one of the further aspects, the liquid dosage forms of the invention may be administered orally or via the oral cavity. The liquid dosage forms of the present invention may also be administered transmucosally, sublingually, via the buccal cavity, via mucosal membranes and/or through the gastrointestinal tract. In one of the further aspects, the liquid dosage forms of the present invention may be administered via pulmonary, intravenous, rectal, ophthalmic, colonic, parenteral, intracisternal, intravaginal, intraperitoneal, local, or topical administration.

In some of the aspects, the liquid dosage forms of the present invention can be given using oral syringe to those patients who cannot take medicine through mouth e.g. patients who have undergone surgery.

In some of the aspects, the liquid dosage forms of the present invention are in the form of spray and may be administered by oral route or nasal route. Sprays are known by various names such as aerosol sprays, liquid pump sprays, or activated mists etc.

In some of the aspects, the liquid dosage forms of the present invention are in the form of immediate release dosage forms or modified release dosage forms, such as extended release, controlled release, sustained release, prolonged release and delayed release. In some of the aspects, the liquid dosage forms comprise Imatinib or pharmaceutically acceptable salt thereof one or more suitable excipients or additives for the preparation of modified release dosage forms such as rate controlling polymers.

The liquid dosage forms of the present invention may also be prepared by reconstitution of dry powder in suitable diluent or media such as water. The dry powder for reconstitution may be in the form of immediate release forms and comprise Imatinib or pharmaceutically acceptable salt thereof and one or more suitable excipients selected form the group comprising of fillers, binders, diluents, disintegrants, pore formers, lubricants, glidants, sweeteners, stabilizing agents, antioxidants, flavoring agents, suspending agents/thickening agents/viscosity modifying agents, surfactants, preservatives and plasticizers. The dry powder for reconstitution may also be in the form of modified release forms and comprise modified release pellets, granules or particles. Such modified release pellets, granules or particles comprise one or more suitable excipients such as rate controlling polymers.

In one of the further aspects, the liquid dosage forms of the invention are suitable for administration to all types of patients' population. In particular, liquid dosage forms of the invention are suitable for pediatric and geriatric patients. The liquid dosage forms of the invention are also useful for the patients who are unable to take solid oral therapy.

In some of the aspects, the pH of the liquid dosage forms of the present invention is between about 2.0 and about 11.0. In some of the aspects, the pH of the liquid dosage forms of the present invention is between about 2.0 and about 7.0. In some of the aspects, the pH of the liquid dosage forms of the present invention is between about 3.0 and about 9.0. In some of the aspects, the pH of the liquid dosage forms of the present invention is between about 4.0 and about 8.0. In some of the aspects, the pH of the liquid dosage forms of the present invention is between about 5.0 and about 7.0. In some of the aspects, the pH of the liquid dosage forms of the present invention is between about 5.5 and about 6.5. In some of the aspects, the pH of the liquid dosage forms of the present invention is between about 3.5 and about 5.0.

In one of the further aspects, the pH of the liquid dosage forms of the present invention is such that prevents the formation of degradants in undesired amounts and provides the liquid dosage forms of the present invention increased stability when stored under storage conditions. In one of the non-limiting aspects, the pH of the liquid dosage forms of the present invention which prevents the formation of degradants in undesired amounts and provides the liquid dosage forms of the present invention increased stability when stored under storage conditions is in the range from about 2.0 to about 7.0.

In one of the further aspects, the liquid dosage forms of the present invention are stable for prolonged time when stored under storage conditions. The term "storage conditions" as used herein without limitation include typical storage conditions such as 2° C.±8° C., 40° C.±2° C./75±5% RH, 30° C.±2° C./65±5% RH, 25° C.±2° C./40±5% RH, 25° C.±2° C./60±5% RH, 40° C.±2° C./NMT 25% RH (NMT=not more than) and accelerated conditions such as 40° C.±2° C./75±5% RH. The term "prolonged time" as used herein indicates that the liquid dosage forms of the present invention are stable for at least 1 month, at least 3 months, at least 6 months or at least 12 months when stored under storage conditions.

As used herein, the terms "stable" or "stability" encompass any characteristic of the liquid dosage forms which may be affected by storage conditions including, without limitation, potency, total impurities, degradation products, specific optical rotation, optical purity, water content, appearance, viscosity, sterility, and colour and clarity. The storage conditions which may affect stability include, for example, duration of storage, temperature, humidity, and/or light exposure.

The term "degradant", "impurity", "degradation impurity" and "related substance" as used herein represents the same meaning and can be used interchangeably.

In some of the aspects of the present invention, "stable" or "storage stable", or "stability" when used with reference to the liquid dosage forms of the present invention or when used "stable liquid dosage forms" or "stability of the liquid dosage forms" all these terms/phrases refer to dosage forms of the present invention which retain at least about 90%, or at least about 95%, or at least about 96%, or at least about 98%, of the labelled concentration of Imatinib or salt thereof contained in the said dosage form after storage under typical and/or accelerated conditions. In further aspects, stable liquid dosage forms or stability of the liquid dosage forms refer to less than about 15% (area percent), or less than about 10% (area percent), or less than about 7% (area percent), or less than about 5% (area percent), or less than about 2% (area percent) of Imatinib-related impurities are present after storage under typical and/or accelerated conditions.

In some of the aspects, liquid dosage forms of the present invention contain no more than about 15% (area percent), or no more than about 10% (area percent), or no more than about 7% (area percent), or no more than about 5% (area percent), or no more than about 2% (area percent), or no more than about 1% (area percent), or no more than about 0.5% (area percent), or no more than about 0.2% (area percent), or no more than about 0.1% (area percent) any known or unknown single Imatinib-related impurity or other impurity after storage under typical and/or accelerated conditions.

In some of the aspects, liquid dosage forms of the present invention contain no more than about 15% (area percent), or no more than about 10% (area percent), or no more than about 7% (area percent), or no more than about 5% (area percent), or no more than about 2% (area percent), or no more than about 1% (area percent), or no more than about 0.5% (area percent), or no more than about 0.2% (area percent), or no more than about 0.1% (area percent) total Imatinib-related impurities or other impurities after storage under typical and/or accelerated conditions.

Methods for determining the stability of the liquid dosage forms of the present invention with respect to a given parameter are well-known to those of skill in the art. For example, individual impurities and total impurities can be assessed by high-performance liquid chromatography (HPLC) or thin layer chromatography (TLC). Unless otherwise indicated to the contrary, a percentage amount of any individual impurities (known/unknown), or total impurities reported herein in the liquid dosage forms are determined by a peak area percent method using HPLC.

The term "comprise/comprises/comprising" as used herein mean that other ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

The term "about," as used herein, refers to any value which lies within the range defined by a variation of up to ±10% of the value.

The use of the terms "a" and "an" and "the" and similar referents in the context of describing the invention (especially in the context of the claims) are to be construed to cover both the singular and the plural, unless otherwise indicated herein or clearly contradicted by context.

All percentages mentioned herein, unless otherwise indicated, are on a w/v basis, i.e. percentage ingredient (active/inactive) present by weight in the total volume of the liquid dosage form.

In accordance with the methods of use and administration of medicinal products, packaging materials, closures and containers vary a great deal and have to meet a wide variety of different requirements. The liquid dosage forms of the present invention may be packaged within any type of pharmaceutically-acceptable package, containers, pumps, bottles with spray pump, bottles with dropper assembly, bottles, collapsible tubes, glass ampoules, stoppered vials, pre-filled syringes, low-density polyethylene (LDPE), high-density polyethylene (HDPE), polyolefin, polypropylene containers/bottles depending upon the quantity of the final dosage form. The bottles or containers without limitation include clear/transparent/opaque or amber colored glass bottles or containers and clear/transparent/opaque or amber colored plastic bottles or containers made from polyethylene, polyamide, polycarbonate, acrylic multipolymers, polypropylene, polyethylene terephthalate, polyvinyl chloride, polystyrene and the like. Depending upon the type of the containers or bottles, closures may have different shapes and sizes. The closure of the packaging material may be made from polyethylene, polyamide, polycarbonate, acrylic multipolymers, polypropylene, polyethylene terephthalate, polyvinyl chloride, polystyrene and the like.

Liquid dosage forms of the present invention may be packaged in a sterile single use bottle/container that contains a unit dose for administration to a patient. Suitable bottles/containers may contain volumes between 1-10 ml, 10-20 ml, 20-40 ml, and 40-100 ml, and even more. The container may typically comprise Imatinib or pharmaceutically acceptable salt thereof in an amount of between 10-40 mg, between 40-80 mg, between 80-130 mg, and even more. Thus, it may also be noted that the container may be a multi-use container (i.e., retains at least one more unit dose after a first unit dose is dispensed).

Following embodiments of the invention describe suitable excipients which may be used to prepare liquid dosage forms of the present invention. It is in no way the intention of the present inventor(s)/applicant(s) to limit the scope of the liquid dosage forms of the present invention by the description of following embodiments. Described embodiments are for illustrative purpose only and a skilled person may use other excipients from the same or different classes as well which may provide liquid dosage forms of the present invention same or improved physico-chemical properties, palatability, stability and the like and retain or increase patients' acceptability towards the therapy. Such other excipients, classes of excipients and compositions resulted therefrom are also part of the present invention and covered within the scope of the present invention.

Vehicles may be used in the liquid compositions of the present invention. Vehicles are the liquid bases that carry drugs and other excipients in dissolved or dispersed state. Vehicles may be aqueous or non-aqueous or mixture thereof. Non-aqueous solvents/co-solvents may also be added in the liquid compositions of the present invention to increase the solubility of poorly soluble substances and enhance the chemical stability of a drug. Suitable solvents/co-solvents, solubilizers or vehicles, that may be employed, in the liquid compositions of the invention include, but are not limited to, dichloromethane, acetonitrile, ethyl acetate, acetone, propylene carbonate, water, glycerine, coconut fatty acid diethanolamide, medium and/or long chain fatty acids or glycerides, monoglycerides, diglycerides, triglycerides, structured triglycerides, soybean oil, peanut oil, corn oil, corn oil monoglycerides, corn oil diglycerides, corn oil triglycerides, polyethylene glycol, caprylocaproylmacroglycerides, caproyl 90, propylene glycol, polyoxyethylenesorbitan fatty acid esters, polyoxyethylene castor oil derivatives, castor oil, cottonseed oil, olive oil, safflower oil, peppermint oil, coconut oil, palm seed oil, beeswax, oleic acid, methanol, ethanol, isopropyl alcohol, butanol, acetone, methyl isobutyl ketone, methyl ethyl ketone and the like or any combinations thereof.

In some of the non-limiting aspects of the present invention, the non-aqueous solvent is glycerin. In some of the further aspects, the glycerin may also act as a stabilizing agent when the liquid dosage forms of the present invention comprise water as vehicle and provide desired stability when stored under storage conditions. In some of the further aspects, the amount of glycerin used to provide desired stability to the liquid dosage forms of the present invention is at least about 25% or more, at least about 30% or more, at least about 40% or more, at least about 50% or more, or at least about 60% or more.

Wetting agents as used herein are routinely used in pharmaceutical formulations, especially in liquid dosage forms to create a homogeneous dispersion of solid particles in a liquid vehicle. This process can be challenging due to a layer of adsorbed air on the particle's surface. Hence, even particles with a high density may float on the surface of the liquid until the air phase is displaced completely. The use of a wetting agent allows removal of adsorbed air and easy penetration of the liquid vehicle into pores of the particle in a short period of time. For an aqueous vehicle, alcohol, glycerin, and PG are frequently used to facilitate the removal of adsorbed air from the surface of particles. Whereas for a non-aqueous liquid vehicle, mineral oil is commonly used as a wetting agent. Non-limiting examples of wetting agents are Benzalkonium chloride, Benzethonium chloride, Cetylpyridinium chloride, Docusate sodium, Nonoxynol 9, Octoxynol, Poloxamer, Poloxamer 124, Poloxamer 188, 237, 338, 407, Polyoxyl 35 castor oil, Polyoxyl 40 hydrogenated castor oil, Polyoxyl 10 oleyl ether, Polyoxyl 20 cetylstearyl ether, Polyoxyl 40 stearate, Polysorbate 20, Polysorbate 40, Polysorbate 60, Polysorbate 80, Sodium lauryl sulfate, Sorbitan monolaurate, Sorbitan monooleate, Sorbitan monopalmitate, Sorbitan monostearate, Tyloxapol and the like or any combinations thereof.

Solubility enhancing agents may include, but are not limited to, DL-methionine, caffeine, nicotinamide, vanillin, benzyl alcohol, ethanol and diethylene glycol monoethyl ether and the like or combinations thereof.

Stabilizing agents may include, but are not limited to, sodium metabisulphite, sodium bisulphite, ethylene diamine tetraacetic acid (EDTA) or salts thereof, ascorbic acid and the like or combinations thereof.

Penetration/permeation enhancers may include, but are not limited to, nicotinamide, caffeine, peppermint oil, sodium glycocholate, phospholipids, alkyl saccharides, aprotinin, benzalkonium chloride, ceramides, cetylpyridinium chloride, chitosan, chitosan-4-thiobutylamidine, cyclodextrins, dextran sulfate, dodecyl azacycloheptyl-2-ketone, ether lipids (plasmologens), glycerol, glycosylated sphingosines, lauric acid, 23-lauryl ether, lysophosphatidyl choline, menthol, methoxysalicylate, phosphatidyl choline, 1-palmitoyl-2-glutaroyl-sn-glycero-3-phosphocholine, polycarbophil cysteine, poly-L-arginine, polyoxyethylene, polyoxyethylene-9-lauryl ether, polysorbate 80, propylene glycol, EDTA, sodium deoxycholate, sodium glycocholate, sodium glycodeoxycholate, sodium lauryl sulfate, sodium salicylate, sodium taurocholate, sodium taurodeoxycholate, sodium taurodihydrofusidate, sphingolipids, sterols and the like or combinations thereof.

Mucoadhesives and/or suspending agents may also be added in the compositions of the present invention. Examples of suitable mucoadhesives include, but are not limited to, hydroxypropyl cellulose, gelatin, crosslinked polyacrylic acid, polymethacrylic acid, polyhydroxyethyl methacrylic acid, hydroxypropyl methyl cellulose, polyethylene glycol, sodium carboxymethyl cellulose, hyaluronic acid, chitosan, polycarbophil, pectin, xanthan gum, alginate, copolymers of dextran, polyacrylamide, acacia, copolymer of caprolactone and ethylene oxide, carbopol 934, tragacanth, eudragit and the like or combinations thereof.

Suspending agents may be natural or synthetic gums or gum derivatives or compounds which swell in the presence of aqueous media.

Stabilizing agents may include, but are not limited to, sodium metabisulphite, sodium bisulphite, ethylene diamine tetraacetic acid (EDTA) or salts thereof, ascorbic acid and the like or combinations thereof.

The pH of an oral liquid formulation is a key point in many regards. Control of the formulation pH, could prevent large changes during storage. Therefore, most formulations utilize a buffer to control potential changes in the solution pH. The amount of buffer capacity needed is generally between 0.01 and 0.1 M, and a concentration between 0.05 and 0.5 M is usually sufficient. The selection of a suitable buffer should be based on (i) Whether the acid-base forms are listed for use in oral liquids, (ii) The stability of the drug and excipients in the buffer, and (iii) The compatibility between the buffer and container. A combination of buffers can also be used to gain a wider range of pH compared to the individual buffer alone. However, not all buffers are suitable for use in oral liquids. For example, a boric acid buffer may be used for optical and IV delivery but not in oral liquids because of its toxicity. The stabilizing effect of buffers that have multiple charged species in solution could also determine the potential reaction between excipients and API. For example, buffers that use carbonates, citrate, tartrate, and various phosphate salts may precipitate with calcium ions by forming sparingly soluble salts. However, this precipitation is dependent upon the solution pH. The activity of phosphate ions may be lowered due to interactions with other solution components.

There are a number of factors that may also affect the solution pH such as temperature, ionic strength, dilution, and the amount and type of co-solvents present. For example, the pH of acetate buffers is known to increase with temperature, whereas the pH of boric acid buffers decreases with temperature. Finally, the drug in solution may itself act as a buffer. If the drug is a weak electrolyte, such as salicylic acid or ephedrine, the addition of base or acid, respectively, will create a system in which the drug can act as a buffer.

One of the most crucial factors involved in formulating a pharmaceutical suspension is the selection of an appropriate suspending agent. Suspending agents impart viscosity, and thus retard particle sedimentation. Other factors considered in the selection of the appropriate agent include desired rheological property, suspending ability in the system, chemical compatibility with other excipients, pH stability, length of time to hydrate, batch-to-batch reproducibility, and cost. Non-limiting examples of pH adjusting agents/modifiers and buffers are Acetic acid, Adipic acid, Ammonium carbonate, Ammonium hydroxide, Ammonium phosphate, Boric acid, Citric acid, Diethanolamine, Fumaric acid, Hydrochloric acid, Malic acid, Nitric acid, Propionic acid, Potassium acetate, Potassium bicarbonate, Potassium chloride, Potassium citrate, Potassium metaphosphate, Potassium phosphate, Sodium acetate, Sodium bicarbonate, Sodium borate, Sodium carbonate, Sodium chloride, Sodium citrate, Sodium glycolate, Sodium hydroxide, Sodium lactate, Sodium phosphate, Sodium proprionate, Succinic acid, Sulfuric acid, Tartaric acid, Triethylamine, Triethanolamine, Tromethamine, Trolamine and the like or any combinations thereof.

In some of the aspects of the present invention, the term "buffering agent" or "buffering agents" may also interchangeably be used with the terms "pH adjusting agent or pH adjusting agents" or "pH modifying agent or pH modifying agents" and vice versa and represents the same meaning.

Suspending agents can be classified into cellulose derivatives, clays, natural gums, and synthetic gums. In many cases, these excipients are used in combination. There are many water soluble hydrocolloids that can act as suspending agents in the formulation of pharmaceutical suspensions. They can be of natural, semi-synthetic or synthetic origin. Non-limiting examples of suspending agents are Acacia, Agar, Alginic acid, Carbomer, Carmellose sodium, Dextrin, Gelatin, Veegum or Gel white, Gellan gum, Sodium alginate, Methylcellulose, Hydroxyethyl cellulose, Hydroxypropyl cellulose, Hydroxypropylmethyl cellulose, Hydroxypropyl starch, Hypromellose, Maltodextrin, Methylcellulose, Modified starch, Pectin, Poloxamer, Polycarbophil, Polyethylene glycol, Polyvinyl acetate, Poly (vinyl alcohol), Potassium alginate, Polyvinyl pyrrolidone, Pregelatinized starch, Propylene glycol alginate, Sodium alginate, Carboxymethyl cellulose or an alkali metal salt thereof, Microcrystalline cellulose, gum Arabic, Karaya gum, Sterculia gum, Tragacanth, Xanthangum, Bentonite, Carageenan, Guar gum, Colloidal silicon dioxide and the like or any combinations thereof.

In some of the non-limiting aspects of the present invention, the suspending agent is present in the liquid dosage forms of the present invention at a concentration which helps to achieve desired dissolution profile of the suspension dosage forms of the present invention.

Microbiological contamination presents a significant health hazard in oral liquids. Therefore, the use of preservatives become inevitable to prevent the growth of microorganisms during the product's manufacture and shelf life, although it may be most desirable to develop a "preservative-free" formulation to address the increasing concerns about the biological activity of these compounds. Most formulations require some kind of preservative to ensure no microbial growth.

The majority of preservatives are bacteriostatic rather than bacteriocidal, and consists of both acid and nonacid types. Among the acidic types are phenol, chlorocresol, 9-phenyl phenol, alkyl esters of para-hydroxybenzoic acid, benzoic acid, boric acid, and sorbic acid, and their respective salts. Therefore, the pH of solution, and the pKa of the preservative need to be carefully evaluated prior to selecting a preservative for a formulation. Neutral preservatives include chlorobutanol, benzyl alcohol, and beta-phenylethyl alcohol. Under alkaline conditions, it is generally regarded that microbial growth is insignificant and at these pH values, the need for a preservative is not generally recommended.

Many preservatives listed in the FDA inactive ingredient guide for liquid dosage forms. Unfortunately, many of them are not recommended for use in oral liquids and hence the choice of an acceptable preservative for an oral liquid formulation is limited. In addition, the solubility of many preservatives in aqueous system may not be high enough for effective antimicrobial activity. Additionally, it is essential to understand that bacteriostatic agents like para hydroxyl benzoic acids can partition between organic and aqueous phases in a heterogenous liquid formulations in such a way that their activity is significantly reduced. Non-limiting examples of preservatives are Alcohol, Ethanol, Chlorobutanol, Phenoxyethanol, Potassium benzoate, Benzyl alcohol, Benzoic acid, Potassium sorbate, Sorbic acid, Benzalkonium chloride, Benzethonium chloride, Cetrimonium bromide, Cetylpyridinium chloride, Bronopol, Chlorbutol, Chlorocresol, Cresol, Butylparaben, Methylparaben, Propylparaben, Ethylparaben, Phenol, Thymol, Phenylethanol, Sodium benzoate, Antimicrobial solvents like Propylene glycol, Glycerin, Chloroform and the like or any combinations thereof. In addition, some formulation ingredients like nonionic surfactants, quaternary ammonium compounds, gelatin, ferric salts, calcium salts and salts of heavy metals, including silver, lead, and mercury prevent microbial growth.

In some of the non-limiting aspects, the liquid dosage forms of the present invention comprise one or more than one preservatives. In some of the further non-limiting aspects, the liquid dosage forms of the present invention comprise combination of two preservatives. In some of the further non-limiting aspects of the present invention, the preservatives are present in the liquid dosage forms of the present invention at a concentration which helps to prevent microbial growth in the liquid dosage forms when stored for prolonged time under storage conditions.

Antioxidants can be compounds that can reduce a drug that has been oxidized, or compounds that are more readily oxidized than the agents they are to protect (oxygen scavengers). Many of the lipid-soluble antioxidants act as scavengers. Antioxidants can also act as chain terminators, reacting with free radicals in solution to stop the free-radical propagation cycle. Mixtures of chelating agents and antioxidants are often used because there appears to be a synergistic effect. This occurs because many of the agents act at differing steps in the oxidative process.

Some substances prone to oxidation include unsaturated oils/fats, compounds with aldehyde or phenolic groups, colors, flavors, sweeteners, plastics and rubbers, the latter being used in containers for products. Oxidation may manifest as products with an unpleasant odour, taste, appearance, precipitation, discoloration or even a slight loss of activity. The term rancidity refers to many typical off-flavors that result from autoxidation of unsaturated fatty acids that are present in oils and fats, and it affects many oils and fats. The distinct rancid odour may result from short-chain, volatile monomers resulting from the cleavage of the longer chain, less volatile oils and fats. Non-limiting examples of antioxidants are α-Tocopherol acetate, Ascorbic acid, Erythorbic acid, Butylated hydroxytoluene (BHT), d-α-Tocopherol natural, Monothioglycerol, Sodium bisulfite, Sodium sulfite, Sodium metabisulfite, Potassium metabisulfite, Acetone sodium bisulfite, Ascorbyl palmitate, Cysteine, d-α-tocopherol synthetic, Nordihydroguaiaretic acid, Sodium formaldehyde sulfoxylate, Sodium thiosulfate, Acetylcysteine, Ascorbyl palmitate, Butylated hydroxyanisole (BHA), Cysteine hydrochloride, Dithiothreitol, Propyl gallate, Thiourea and the like or any combinations thereof.

In some instances, there are insufficient drug particles in a unit dose of suspension to make a pharmaceutically elegant suspension. This is particularly true for the more highly active drugs, where the unit dose is small. Under such circumstances, the formulator will need to add more particles to improve the appearance of the final product, and also to help stabilize the suspension. To serve this purpose, bulking agents, also known as auxiliary suspending agents are used. Non-limiting examples of bulking agents are Calcium carbonate, Calcium hydroxide, Cellulose, Crospovidone, Dibasic calcium phosphate, Magnesium carbonate, Magnesium hydroxide, Microcrystalline cellulose, Silica (silicon dioxide), Titanium dioxide and the like or any combinations thereof.

Many different materials are capable of adsorbing onto the suspended particles, e.g. natural gums, cellulosics and non-ionic surfactants. However, not all of them are able to act as protective colloids and provide steric hindrance to caking at a sufficiently low concentration. High levels of surfactants, for example, can increase gastro-intestinal motility. Higher molecular weight gums and cellulosics may also cause an unacceptable increase in the viscosity of the system. There are, however, certain polymers, or grades of polymers, that are capable of acting as protective colloids at concentrations that do not markedly increase the viscosity of the system, or increase gut motility, etc. Such materials include poloxamers, lower molecular weight grades of povidone, and low molecular weight grades of some other hydrophilic colloids.

Surfactant is a general name for materials that possess surface activity; in solution they tend to orient at the surface of the liquid. There are several general classes of surfactants: anionic, cationic, amphoteric and non-ionic. Surfactants are amphiphilic molecules, i.e. part of the molecule is hydrophilic, and part is lipophilic. This combination of the two opposite affinities in the same molecule causes them to orient to the interface and thereby reduce the interfacial tension between the continuous and disperse phases, such as in emulsions and suspensions. Ionic surfactants work primarily through electrostatic forces, whereas non-ionic surfactants work primarily through steric forces. Non-limiting examples of surfactants are Sodium lauryl sulfate, Docusate sodium, Cocamidopropyl amino betaine, Polyoxyethylene sorbitan fatty acid esters (Polysorbate, Tween®), Polyoxyethylene 15 hydroxystearate (Macrogol 15 hydroxystearate, Solutol HS15®), Polyoxyethylene castor oil derivatives (Cremophor® EL, ELP, RH 40), Polyoxyethylene stearates (Myrj®)), Sorbitan fatty acid esters (Span®), Polyoxyethylene alkyl ethers (Brij®), Polyoxyethylene nonylphenol ether (Nonoxynol®) and the like or any combinations thereof.

Anti-foaming agents may be used in the preparation of the liquid pharmaceutical compositions of the present invention to lower the surface tension and cohesive binding of liquid phase. Non-limiting examples of anti-foaming agents are simethicone, organic phosphates, alcohols, paraffin oils, stearates, glycols and the like or any combinations thereof.

Chelating agents, also known as sequestrants, are molecules that have the ability to form stable complexes with metal ions, particularly di-valent and tri-valent metal ions including trace metals and heavy metals. These metal ions are often implicated in API degradation by acting as catalysts, e.g. $Mg^{2+}$ will catalyze both ester hydrolysis and the Maillard interaction between primary or secondary amines and reducing sugars. Oxidative degradation is also often catalyzed by heavy metals. In addition, certain trace metals are required for microbial growth, and chelation (sequestration) to form complexes can help prevent microbial growth and spoilage, and thus allow lower levels of microbiocidal agents to be used. Non-limiting examples of chelating agents are Calcium disodium edetate, Disodium edetate, Edetic acid (also known as ethylenediaminetetraacetic acid/EDTA), Citric acid and the like or any combinations thereof.

Palatability of oral medicines is an important factor in compliance. There are several components to palatability including flavor, mouth-feel and sweetness. Most patients prefer medicines that are not too bitter but may be slightly "tart" (acidic). Most APIs are bitter. However, for bitterness to develop, the drug must be sufficiently soluble to interact with taste receptors on the tongue. For insoluble APIs in the form of suspensions, components of the suspension are also bitter, e.g. preservatives, or very salty, e.g. buffer systems. However, a slight saltiness and a slight bitterness are desirable for palatability.

Traditionally, oral medicines were sweetened using Syrup (concentrated sucrose solution) or honey (contains fructose). However, these materials are inadequate for the formulation of many products because they simply are not able to adequately mask the very bitter taste of many pharmaceutical materials, including APIs and excipients. Several alternative sweetening agents have been developed over the years to better mask unpleasant tastes in both processed foods and pharmaceuticals.

Several of the materials classified as sweetening agents are sugar alcohols (also known as polyhydric alcohols, polyols and hydrogenated sugars). Several of the commonly used sweetening agents are ionic and have the potential to interact with other components of the suspension. Some sweetening agents are more stable than others in aqueous solution. These will be important factors in the final selection of the sweetening agent. Non-limiting examples of sweetening agents are Glucose, Sucralose, Trehalose, Fructose, Xylose, Dextrose, Galactose, Tagatose, Maltose, Sucrose, Glycerol, Dulcitol, Mannitol, Lactitol, Sorbitol, Xylitol, Saccharine or the corresponding sodium, potassium or calcium salt, Cyclamate or the corresponding sodium or calcium salt, Aspartame, or Acesulfame or the potassium salt thereof, Dulcin or Ammonium glycyrrhizinate, Alitame, Inulin, Isomalt, Neohesperidin dihydrochalcone, Thaumatin and the like or any combinations thereof.

Flavors are used to improve the palatability of oral medicines. One problem that can arise with oral suspensions is that the suspension may produce a "cloying" sensation in the mouth. While this is not the same as a bitter taste, it can nevertheless cause problems for the patient and affect compliance. This can be a particular problem with high levels of inorganic components. Flavors can help reduce this "cloying" taste and thereby improve palatability, and ultimately patient compliance.

There are many different flavors, and most flavors are complex mixtures of many components. Today most flavors are developed by specialist flavor houses, and typically the flavor is formulated for each individual application. Since flavor will be part of the suspension continuous phase, it has the maximum potential for interaction, and some flavor components may cause stability issues (physical or chemical) for the suspension. Flavor development and compounding is a specialist discipline. When deciding on which particular flavor is appropriate, the flavor specialist would benefit from knowledge of the other likely components in the suspension, just as the formulation scientist would benefit from knowledge of the components of the flavor.

Flavors can adsorb onto finely divided solids, thus reducing their effectiveness. They can also be absorbed by packaging. Flavor preferences vary with age, but the citrus flavors appear generally acceptable to most age groups. Non-limiting examples of flavoring agents are synthetic flavor oils and flavoring aromatics and/or natural oils, extracts from plants leaves, flowers, fruits, and so forth and the like or any combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth and the like or any combinations thereof. Solid forms, such as spray dried forms of flavoring agents, may also be useful in the liquid dosage forms disclosed herein.

Coloring agents may also be used in the preparation of the liquid compositions of the present invention. Pharmaceutical colors come in two types; soluble dyes and insoluble pigments. For pharmaceutical suspensions intended for oral use, soluble dyes are often used; however, pigments may also be used and would be part of the disperse phase. Soluble dyes have the potential to interact with other components of the formulation.

In some of the aspects, the liquid dosage forms of the present invention are non-caking liquid dosage forms. The term "non-caking" as used herein means that the liquid dosage form has a smooth consistency and doesn't contain any caking or clumping particles, by visual inspection. Also, the liquid dosage form in accordance with the present invention does not cake or clump during manufacture, i.e., when mixed with excipients. Nor does it cake or clump upon storage, even under relatively humid conditions, e.g., a relative humidity of about 75% or greater and when stored for relatively long periods such as about 6 months or longer and even at elevated temperatures of about 40° C. or greater, or at any combination of such humidity, time and temperature parameters. Thus, the liquid dosage forms in accordance with the present invention will remain non-caking during typical storage and use conditions. "Imatinib" as used herein, unless the context requires otherwise, includes Imatinib, its pharmaceutically acceptable salts and chemical derivatives thereof such as polymorphs, solvates, hydrates, anhydrous forms, amorphous forms, prodrugs, chelates, and complexes. "Imatinib" as used herein also includes racemic or substantially pure forms.

In one of the further aspects, Imatinib or pharmaceutically acceptable salt thereof used for the preparation of the liquid dosage forms of the present invention comprise particles of Imatinib or pharmaceutically acceptable salt thereof, wherein the $d_{90}$ of the particles of Imatinib or pharmaceutically acceptable salt thereof is less than about 1000 μm, or less than about 950 μm, or less than about 900 μm, or less than about 850 μm, or less than about 800 μm, or less than about 750 μm, or less than about 700 μm, or less than about 650 μm, or less than about 600 μm, or less than about 550 μm, or less than about 500 μm, or less than about 450 μm, or less than about 400 μm, or less than about 350 μm, or less than about 300 μm, or less than about 250 μm, or less than about 200 μm, or less than about 150 μm, or less than about 100 μm, or less than about 90 μm, or less than about 80 μm, or less than about 70 μm, or less than about 60 μm, or less than about 50 μm, or less than about 40 μm, or less than about 30 μm, or less than about 20 μm, or less than about 10 μm, or less than about 5 μm, or less than about 2 μm, or less than about 1 μm, or less than about 0.5 μm.

In one of the further aspects, the liquid dosage forms of the present invention comprise particles of Imatinib or pharmaceutically acceptable salt thereof, wherein the $d_{90}$ of the particles of Imatinib or pharmaceutically acceptable salt thereof is less than about 1000 μm, or less than about 950 μm, or less than about 900 μm, or less than about 850 μm, or less than about 800 μm, or less than about 750 μm, or less than about 700 μm, or less than about 650 μm, or less than about 600 μm, or less than about 550 μm, or less than about 500 μm, or less than about 450 μm, or less than about 400 μm, or less than about 350 μm, or less than about 300 μm, or less than about 250 μm, or less than about 200 μm, or less than about 150 μm, or less than about 100 μm, or less than about 90 μm, or less than about 80 μm, or less than about 70 μm, or less than about 60 μm, or less than about 50 μm, or less than about 40 μm, or less than about 30 μm, or less than about 20 μm, or less than about 10 μm, or less than about 5 μm, or less than about 2 μm, or less than about 1 μm, or less than about 0.5 μm.

In one of the aspects, general formula of the liquid dosage forms according to the present invention may be provided as follows.

TABLE 1

General formula of liquid dosage forms of the present invention

| | | Quantity (% w/v) | |
|---|---|---|---|
| Sr No | Ingredient | Solution dosage form | Suspension dosage form |
| 1 | Imatinib or pharmaceutically acceptable salt thereof (active ingredient) | 0.01-25 | 0.01-25 |
| 2 | Suspending agent(s)/thickening agent(s)/viscosity modifying agent(s) | — | 0.01-10 |
| 3 | Preservative(s) | 0.01-10 | 0.01-10 |
| 4 | Wetting agent(s) | — | 0-90 |
| 5 | pH adjusting agent(s)/pH modifying agents | Q.S. to adjust the pH | Q.S. to adjust the pH |
| 6 | Buffering agent(s) | Q.S. to adjust the pH | Q.S. to adjust the pH |
| 7 | Solvent(s)/co-solvent(s) | Q.S. | Q.S. |
| 8 | Solubilizer(s) | Q.S. | Q.S. |
| 9 | Anti-foaming agent(s) | — | 0.01-10 |
| 10 | Anti-caking agent(s) | — | 0-10 |
| 11 | Antioxidant | — | 0-10 |
| 12 | Surfactant(s) | 0-10 | 0.01-10 |
| 13 | Sweetening agent(s) | 0.01-15 | 0.01-50 |

TABLE 1-continued

General formula of liquid dosage forms of the present invention

| Sr No | Ingredient | Quantity (% w/v) Solution dosage form | Suspension dosage form |
|---|---|---|---|
| 14 | Flavoring agent(s) | 0.01-5 | 0.01-5 |
| 15 | Coloring agent(s) | 0-2 | 0-2 |
| 16 | Vehicle(s) | Q.S. | Q.S. |

Q.S. = Quantity Sufficient

Those who are skilled in the art will appreciate that different types of liquid dosage forms as described herein can be prepared by using suitable excipients or additives known in the art. Thus, the name of excipients or additives and proportionate range thereof provided in the Table-1 is provided herein for the illustration purpose only and should not be construed as the exact or the only scope of the present invention. The liquid dosage forms of the present invention may be prepared using suitable excipients or additives in any suitable amount.

In one of the further aspects, the present invention provides process for the preparation of the liquid dosage forms of Imatinib or pharmaceutically acceptable salt thereof.

Process-1: Preparation of Solution Dosage Forms
1. Add one or more sweetener(s) followed by one or more preservative(s) in the suitable vehicle;
2. Add Imatinib or pharmaceutically acceptable salt thereof;
3. Add one or more buffering agent(s) to adjust the desired pH followed by flavoring agent; and
4. Adjust the volume to the required quantity with vehicle.

Process-2: Preparation of Solution Dosage Forms
1. Add one or more solvent(s) followed by one or more sweetener(s) and one or more preservative(s) in the suitable vehicle;
2. Add Imatinib or pharmaceutically acceptable salt thereof;
3. Add one or more buffering agent(s) to adjust the desired pH followed by flavoring agent; and
4. Adjust the volume to the required quantity with vehicle.

Process-3: Preparation of Suspension Dosage Forms
1. Add one or more preservative(s) followed by one or more buffering agent(s) to adjust the desired pH in the suitable vehicle;
2. Add one or more sweetener(s) and flavoring agent followed by one or more suitable solvent(s)/co-solvent(s) and/or one or more solubilizer(s);
3. Add one or more suspending agent(s) followed by one or more anti-foaming agent(s) and one or more surfactant(s);
4. Add Imatinib or pharmaceutically acceptable salt thereof; and
5. Adjust the volume to the required quantity with vehicle.

Process-4: Preparation of Suspension Dosage Forms
1. Add and mix one or more solubilizer(s) in the suitable vehicle;
2. Add one or more suspending agent(s);
3. Add one or more antioxidant(s) and one or more sweetener(s) dissolved in the suitable solvent(s) to step (2);
4. Add Imatinib or pharmaceutically acceptable salt thereof; and
5. Add flavoring agent and adjust the volume to the required quantity with vehicle.

Those who are skilled in the art can understand that some variations in the process described herein can be adopted. A skilled person may omit use of some pharmaceutical excipients as described herein above. A skilled person may also alternatively use some or all pharmaceutical excipients as described herein from the same excipient classes. Such variations are well within the scope of the present invention. A skilled person can also change and/or omit steps of their sequences of the herein described process for the purposes of suitability and convenience where one or more pharmaceutically acceptable excipients may or may not be used without affecting and diminishing the quality and characteristics of the resulting product. Such variations/changes/omissions/additions are well within the scope of the present invention.

The liquid dosage forms of the present invention may also be prepared using processes generally known to those skilled in the art. The processes for the preparation of liquid dosage forms of the present invention may vary depending upon the final dosage form, e.g. solution, suspension, etc. The processes for the preparation of the liquid dosage forms of the present invention may comprise multiple steps. Such steps may include sequential addition of suitable excipients/additives. Such steps may also include physical processes for example mixing, stirring, agitation etc.

In one of the aspects, the liquid dosage forms of the present invention are suitable for administration to a subject to treat or prevent a disease or condition. Preferably, the subject is a mammal. More preferably, the mammal is a human. Preferably, the disease or condition is a disease or condition that is treatable by the administration of Imatinib or pharmaceutically acceptable salt thereof.

In one of the aspects, the present invention is directed to the method for the treatment of a disease or disorder or medical condition that can be treated by inhibiting protein-tyrosine kinase comprising administering to a patient, such as human, an effective dosage amount of a liquid dosage form comprising Imatinib or pharmaceutically acceptable salt thereof and one or more pharmaceutically acceptable excipients or additives as disclosed and described herein.

In one of the further aspects, the present invention is directed to the method for the treatment of a tumor disease or cancer disease, including without limitation, colon cancer, thyroid cancer, ovarian cancer, breast cancer, lung cancer (non-small cell lung cancer), head and neck cancer, uterine cancer, non-hodgkin lymphoma, blood cancer, skin cancer, prostate cancer, kidney cancer, rectal cancer, peritoneal cavity cancer, brain cancer, gastric cancer, metastatic cancer, colorectal cancer, pancreatic cancer, endometrial cancer, stomach cancer, gastrointestinal cancer, bladder cancer, and the like comprising administering to a patient, such as human, an effective dosage amount of a liquid dosage form comprising Imatinib or pharmaceutically acceptable salt thereof and one or more pharmaceutically acceptable excipients or additives as disclosed and described herein.

In one of the further aspects, the present invention is directed to the method for the treatment of at least one disease or condition selected from the group comprising of chronic myeloid leukemia, acute lymphoblastic leukemia, myelodysplastic diseases, myeloproliferative diseases, aggressive systemic mastocytosis, hypereosinophilic syndrome and/or chronic eosinophilic leukemia, unresectable, recurrent and/or metastatic dermatofibrosarcoma protuberans, and unresectable and/or metastatic malignant gastrointestinal stromal tumors comprising administering to a patient, such as human, an effective dosage amount of a liquid dosage form comprising Imatinib or pharmaceutically acceptable salt thereof and one or more pharmaceutically acceptable excipients or additives as disclosed and described herein.

"Effective dosage amount" as used herein with respect to, for example Imatinib liquid dosage forms shall mean that dosage that provides the specific pharmacological response for which Imatinib administered in a significant number of subjects in need of such treatment. It is emphasized that "effective dosage amount", administered to a particular subject in a particular instance will not always be effective in treating the diseases described herein, even though such dosage is deemed a "effective dosage amount" by those skilled in the art.

In one of the further aspects, the present invention is directed to use liquid dosage forms of the present invention for the treatment of a disease or disorder that can be treated by inhibiting protein-tyrosine kinase. In one of the further aspects, the present invention is directed to use liquid dosage forms of the present invention for the treatment of a tumor disease or a cancer disease, including without limitation, colon cancer, thyroid cancer, ovarian cancer, breast cancer, lung cancer (non-small cell lung cancer), head and neck cancer, uterine cancer, non-hodgkin lymphoma, blood cancer, skin cancer, prostate cancer, kidney cancer, rectal cancer, peritoneal cavity cancer, brain cancer, gastric cancer, metastatic cancer, colorectal cancer, pancreatic cancer, endometrial cancer, stomach cancer, gastrointestinal cancer, bladder cancer, and the like.

In one of the further aspects, the present invention is directed to use liquid dosage forms of the present invention for the treatment of at least one diseases or condition selected from the group comprising of chronic myeloid leukemia, acute lymphoblastic leukemia, myelodysplastic diseases, myeloproliferative diseases, aggressive systemic mastocytosis, hypereosinophilic syndrome and/or chronic eosinophilic leukemia, unresectable, recurrent and/or metastatic dermatofibrosarcoma protuberans, and unresectable and/or metastatic malignant gastrointestinal stromal tumors.

The liquid dosage forms of the present invention are proposed to have unexpectedly dramatic dissolution profiles. Rapid dissolution of an administered active agent is preferable, as faster dissolution generally leads to greater bioavailability and faster onset of action. To improve the dissolution profile and bioavailability of Imatinib it would be useful to increase Imatinib's dissolution so that it could attain a level close to 100% dissolution of the drug substance.

The liquid dosage forms of the present invention comprising Imatinib or a pharmaceutically acceptable salt thereof, exhibit improved or comparable pharmacokinetic profiles as compared to known Imatinib compositions, e.g. Gleevec®. For example, the Cmax and/or AUC of the liquid dosage forms of Imatinib of the present invention can be greater than or substantially equal to the Cmax and/or AUC for known Imatinib compositions administered at the same dose. In addition, the Tmax of the liquid dosage forms of Imatinib of the present invention can be lower than or substantially equal to that obtained for a known Imatinib compositions, administered at the same dose. In addition, combinations of an improved or comparable Cmax, AUC and Tmax profile can be exhibited by the liquid dosage forms of Imatinib of the invention, as compared to known Imatinib compositions. In further aspects, the liquid dosage forms of Imatinib of the present invention may result in minimal different absorption levels when administered under fed as compared to fasting conditions.

In one of the aspects, a liquid dosage form comprising Imatinib or pharmaceutically acceptable salt thereof exhibits in comparative pharmacokinetic testing with an Imatinib marketed or known formulation, administered at the same dose, a Tmax not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the Tmax exhibited by the marketed or known Imatinib formulation.

In one of the further aspects, the liquid dosage form comprising Imatinib or pharmaceutically acceptable salt thereof exhibits in comparative pharmacokinetic testing with an Imatinib marketed or known formulation, administered at the same dose, a Cmax which is at least about 50%, at least about 100%, or at least about 150%, greater than the Cmax exhibited by the marketed or known Imatinib formulation. In one of the further aspects, the liquid dosage form comprising Imatinib or pharmaceutically acceptable salt thereof exhibits in comparative pharmacokinetic testing with an Imatinib marketed or known formulation, administered at the same dose, a Cmax which is in the range between about 70% and about 150%.

In one of the further aspects, the liquid dosage form comprising Imatinib or pharmaceutically acceptable salt thereof exhibits in comparative pharmacokinetic testing with an Imatinib marketed or known formulation, administered at the same dose, an AUC which is at least about 25%, at least about 50%, at least about 75%, at least about 100%, at least about 125%, at least about 150%, at least about 175%, or at least about 200%, greater than the AUC exhibited by the marketed or known Imatinib formulation. In one of the further aspects, the liquid dosage form comprising Imatinib or pharmaceutically acceptable salt thereof exhibits in comparative pharmacokinetic testing with an Imatinib marketed or known formulation, administered at the same dose, an AUC which is in the range between about 80% and about 125%.

In one of the further aspects, the Tmax of Imatinib or salt thereof, when assayed in the plasma of the mammalian subject, is less than about 6 to about 8 hours. In other aspects of the invention, the Tmax of Imatinib or salt thereof is less than about 6 hours, less than about 5 hours, less than about 4 hours, less than about 3 hours, less than about 2 hours, less than about 1 hour, or less than about 30 minutes after administration.

In some aspects, the liquid dosage forms of Imatinib of the present invention exhibit improved or comparable bioavailability as compared to known Imatinib compositions, e.g. Gleevec®.

The present invention is further exemplified by the following non-limiting examples.

Best Mode of Carrying Out the Invention

EXAMPLES

The liquid dosage forms of the present invention are explained in more detail with reference to the following examples. These examples are provided by way of illustration only and should not be construed as to limit the scope or spirit of the claims in any manner.

Examples 1-4: Preparation of Solution Dosage Forms of Imatinib

TABLE 2

Examples of Imatinib solution dosage forms (without glycerine)

| Ingredients | Example 1 | Example 2 | Example 3 |
|---|---|---|---|
| | Quantity (mg/mL) | | |
| Imatinib mesylate | 95.6 (free base = 80.0) | 95.6 (free base = 80.0) | 95.6 (free base = 80.0) |
| Liquid maltitol | 300.0 | 300.0 | 300.0 |
| Methyl paraben | 5.0 | 5.0 | 5.0 |
| Ethyl paraben | 1.0 | 1.0 | 1.0 |
| Citric acid | Q.S. to desired pH | Q.S. to desired pH | Q.S. to desired pH |
| Sodium citrate | Q.S. to desired pH | Q.S. to desired pH | Q.S. to desired pH |
| Strawberry flavour | 0.1 | 0.1 | 0.1 |
| Purified Water | Q.S. to 1 mL | Q.S. to 1 mL | Q.S. to 1 mL |

Q.S. = Quantity sufficient; desired pH = between about 2.0 to about 7.0

Method of Preparation:
1. Take required quantity of water;
2. Dissolve required quantity of Methyl paraben and Ethyl paraben in water. If required mixture may be heated to dissolve Methyl paraben & Ethyl paraben and cooled down;
3. Add required quantity of Liquid maltitol and mix till get homogenously mixed;
4. Add required quantity of Imatinib mesylate and mix till completely dissolved;
5. Add Citric acid and Sodium citrate till desired pH is attained;
6. Add required quantity of Strawberry flavour and mix till completely dissolved; and
7. Make up the final desired volume with water.

TABLE 3

Stability data at different stability conditions of different Imatinib liquid compositions

| | Stability condition | pH | Single maximum impurity (Unknown) NMT 0.2% | Total impurities NMT 1.0% | Freeze-thaw study observation (Freezer −10° C. to −20° C. for 2 days) |
|---|---|---|---|---|---|
| Example 1 | Initial | 3.48 | 0.02 | 0.57 | Do not freeze but dark brownish colour observed |
| | 3M 40° C./25% RH | 3.47 | 0.02 | 0.57 | |
| | 3M 25° C./40% RH | 3.48 | 0.02 | 0.57 | |
| Example 2 | Initial | 4.31 | 0.03 | 0.66 | Product was precipitated out |
| | 3M 40° C./25% RH | 4.31 | 0.03 | 0.69 | |
| | 3M 25° C./40% RH | 4.27 | 0.03 | 0.66 | |
| Example 3 | Initial | 5.05 | 0.02 | 0.63 | Product was precipitated out |
| | 3M 40° C./25% RH | 5.05 | 0.03 | 0.65 | |
| | 3M 25° C./40% RH | 5.03 | 0.03 | 0.62 | |

NMT = Not more than

TABLE 4

Imatinib solution dosage form (with glycerine)

| Ingredients | Example-4 Quantity (mg/mL) |
|---|---|
| Imatinib Mesylate | 95.6 (free base = 80.0) |
| Liquid maltitol | 100.0 |
| Glycerine | 300.0 |
| Sodium benzoate | 0.2 |
| Acesulfame potassium | 1.0 |
| Citric acid monohydrate | Q.S. to desired pH |
| Strawberry flavour | 0.1 |
| Purified Water | Q.S. to 1 mL |

Q.S. = Quantity sufficient; desired pH = between about 2.0 to about 7.0

TABLE 5

Imatinib solution dosage form (with glycerine)

| Ingredients | Example-4 Quantity (mg/mL) |
|---|---|
| Imatinib mesylate | 1-1000 |
| Liquid maltitol | 0-500 |
| Glycerin | 250-800 |
| Sodium benzoate | 0-1.0 |
| Acesulfame potassium | 0.01-10 |
| Citric acid monohydrate | Q.S. to desired pH |
| Strawberry flavour | 0.01-10 |
| Purified water | Q.S. to 1 mL |

Q.S. = Quantity sufficient desired pH = from about 2.0 to about 7.0

Method of Preparation:
1. Take required quantity of purified water;
2. Add required quantity of Glycerin and mix till get homogenously mixed;
3. Add required quantity of Liquid maltitol and mix till get homogenously mixed;
4. Add required quantity of Sodium benzoate and mix till completely dissolved;
5. Add required quantity of Acesulfame potassium and mix till completely dissolved;
6. Add required quantity of Imatinib mesylate and mix till completely dissolved;

7. Add Citric acid till desired pH is attained;
8. Add required quantity of Strawberry flavour and mix till completely dissolved; and
9. Make up the final desired volume with Water.

TABLE 6

Stability data of Example 4

| Stability conditions | | pH | Single maximum impurity (Unknown) NMT 0.2% | Total impurities NMT 1.0% |
|---|---|---|---|---|
| Initial | | 4.44 | ND | ND |
| | 1M | 4.4 | ND | ND |
| 40° C. ± 2° C./ | 2M | 4.42 | 0.08 | 0.37 |
| 25% RH | 3M | 4.64 | 0.06 (RRT 0.68) | 0.63 |
| | 6M | 4.6 | 0.07 (RRT 0.68) | 0.69 |
| 25° C. ± 2° C./ | 3M | 4.55 | 0.06 (RRT 0.68) | 0.55 |
| 40 ± 5% RH | 6M | 4.55 | 0.06 (RRT 0.68) | 0.57 |

ND = Not detected; NMT = Not more than

Example 5: Preparation of Suspension Dosage Form of Imatinib

TABLE 7

Example of Imatinib suspension dosage form

| Ingredients | Function | Quantity (mg/mL) |
|---|---|---|
| Imatinib or salt thereof | Active ingredient | 10-200 |
| Methyl paraben | Preservative | 0.1-5.0 |
| Ethyl paraben | Preservative | 0.1-5.0 |
| Xanthan gum | Suspending agent/ viscosity builder | 0.1-10 |
| Sorbitol solution | Sweetener | 0.1-500 |
| Flavor | Flavoring agent | 0.1-50 |
| Glycerin | Solvent or co-solvent/ Wetting agent | 0-900 |
| Disodium hydrogen phosphate dihydrate | Buffering agent | 1-50 |
| Sodium dihydrogen phosphate dihydrate | Buffering agent | 1-50 |
| Simethicone | Anti-foaming agent | 0.01-20 |
| Polysorbate 80 | Surfactant/ wetting agent | 0-20 |
| Purified water | Vehicle | Q.S. to 1 mL | pH = between about 5.0 and about 8.5
Q.S. = Quantity sufficient

Method of Preparation:
1. Take required quantity of purified water;
2. Add methyl paraben and ethyl paraben and mix till get dissolved, heating may be required, if necessary;
3. Add disodium hydrogen phosphate dihydrate and sodium dihydrogen phosphate dihydrate and mix till get dissolved;
4. Add sorbitol solution and flavor and mix till get dissolved;
5. Add glycerin and mix till get dispersed;
6. Add xanthan gum and mix till get dispersed;
7. Add simethicone and polysorbate 80 one by one and mix till get dispersed;
8. Add Imatinib or salt thereof and mix to form homogenous suspension; and
9. Adjust the final quantity with purified water.

Example 6: Preparation of Suspension Dosage Form of Imatinib

TABLE 8

Example of Imatinib suspension dosage form

| Ingredients | Quantity (mg/mL) |
|---|---|
| Imatinib or salt thereof | 10-200 |
| Ethanol (absolute) | 0.001-0.5 (mL) |
| Butylated hydroxyl toluene (BHT) | 0.01-1.0 |
| Sucralose | 0.1-25 |
| Colloidal silicon dioxide | 1-50 |
| Flavor | 0.1-25 |
| Caprylocaproyl macrogo 8 glycerides | 1-200 |
| Medium chain triglyceride | Q.S. to 1 mL |

Method of Preparation:
1. Add required quantity of medium chain triglyceride;
2. Add and mix caprylocaproyl macrogol 8 glycerides till get uniformly dispersed;
3. Add and mix colloidal silicon dioxide till get uniformly dispersed;
4. Add butylated hydroxy toluene (BHT) and sucralose dissolved in ethanol mixture to step (3);
5. Add Imatinib or salt thereof; and
6. Add flavour and make up volume with medium chain triglycerides.

Example 7: Bio-Equivalency Study of the Liquid Dosage Forms of the Present Invention Prepared According to Example 4

The liquid dosage forms prepared according to Example 4 of the present invention were tested for its bio-equivalence against the reference product, i.e. Gleevec® marketed tablets. The results of the bio-equivalence study shows that the liquid dosage forms of the present invention have improved and/or comparable pharmacokinetic profile and/or bioavailability when compared against the known Imatinib formulations. The results are summarized in the table below.

TABLE 9

Bio-equivalence study results

| | Cmax | Tmax | $AUC_t$ | $K_{ele}$ | $T_{1/2}$ | $AUC^\infty$ | AUC_ratio |
|---|---|---|---|---|---|---|---|
| Mean | 2170.34 | 2.81 | 34479.46 | 0.05 | 14.80 | 35929.20 | 96.00 |
| SD | 800.16 | 0.98 | 13581.91 | 0.01 | 3.08 | 14259.21 | 0.29 |

| Parameters | Geometric Mean (Test) | Geometric Mean (Reference) | T/R Ratio | Power | Intra % CV | Inter % CV | Lower confidence interval | Upper confidence interval |
|---|---|---|---|---|---|---|---|---|
| LAUCt | 33498.56 | 32140.21 | 104.23 | 100.00 | 13.74 | 36.48 | 98.15 | 110.68 |
| LCmax | 2149.35 | 2044.66 | 105.12 | 100.00 | 12.65 | 32.05 | 99.46 | 111.10 |

Example 8: Effect of Co-Solvent on the Liquid Dosage Forms of the Present Invention

| Composition Test Parameters | 9.56% Imatinib mesylate + 10% liquid maltitol + 20% glycerin + sodium benzoate + acesulfame potassium + citric acid monohydrate + strawberry flavor + water (the composition freezed after 1$^{st}$ cycle) | | | 9.56% Imatinib mesylate + 10% liquid maltitol + 15% glycerin + 15% polyethylene glycol + sodium benzoate + acesulfame potassium + citric acid monohydrate + strawberry flavor + water (freezed) | | | 9.56% Imatinib mesylate + 10% liquid maltitol + 30% polyethylene glycol + sodium benzoate + acesulfame potassium + citric acid monohydrate + strawberry flavor + water (freezed) | | |
|---|---|---|---|---|---|---|---|---|---|
| | Initial | 60° C. 7 days | Freeze thaw Cycle III (clear solution) | Initial | 60° C. 7 days | Freeze thaw Cycle III (freezed) | Initial | 60° C. 7 days | Freeze thaw Cycle III (freezed) |
| Related substances | | | | | | | | | |
| RRT-0.48 | 0.08% | 0.09% | 0.08% | 0.09% | 0.09% | 0.08% | 0.09% | 0.08% | 0.07% |
| RRT-0.59 | 0.03% | 0.03% | 0.03% | 0.03% | 0.03% | 0.03% | 0.03% | 0.03% | — |
| RRT-0.66 | — | — | — | — | — | — | — | — | — |
| RRT-0.67 | — | — | — | — | — | — | — | — | — |
| RRT-0.68 | 0.09% | 0.07% | 0.05% | 0.09% | 0.07% | 0.04% | 0.09% | 0.08% | 0.06% |
| RRT-0.90 | — | — | — | — | 0.03% | — | — | 0.03% | — |
| RRT-0.95 | — | — | — | — | 0.03% | — | — | 0.03% | — |
| RRT-1.20 | 0.12% | 0.13% | 0.12% | 0.13% | 0.13% | 0.13% | 0.13% | 0.12% | 0.11% |
| RRT-1.43 | — | — | — | — | — | — | — | — | — |
| Total impurities | 0.34% | 0.43% | 0.40% | 0.44% | 0.49% | 0.47% | 0.40% | 0.42% | 0.37% |

RRT = Relative retention time

From above data it can be concluded that the liquid dosage form comprising only glycerin does not freeze after gone through freeze-thaw cycles whereas the liquid dosage forms comprising (i) mixture of glycerin and polyethylene glycol and (ii) only polyethylene glycol gets freezed after gone through freeze-thaw cycle (for further data see Table-10 below). Thus, glycerin is the preferred solvent/co-solvent/solubilizer according to the present invention and at least 25% or more glycerin is required to achieve optimum results.

Example-9: Free-Thaw Study and Super Accelerated Stability Study of Different Liquid Dosage Forms Prepared

TABLE 10

| Freeze-thaw cycle data of different liquid dosage forms | | | | |
|---|---|---|---|---|
| Composition | Batch No. | Cycle 1 Freezer (−10° C. to −20° C.) | Cycle 2 Freezer (−10° C. to −20° C.) | Cycle 3 Freezer (−10° C. to −20° C.) |
| 9.56% Imatinib mesylate + 10% liquid maltitol + 20% glycerin + sodium benzoate + acesulfame potassium + citric acid monohydrate + strawberry flavor + water | INBL2050 | Slightly freezed | Clear solution- not freezed | Clear solution- not freezed |
| 9.56% Imatinib mesylate + 10% liquid maltitol + 15% glycerin + 15% polyethylene glycol + sodium benzoate + acesulfame potassium + citric acid monohydrate + strawberry flavor + water | INBL2056 | Clear solution- not freezed | Slightly freezed | Freezed |
| 9.56% Imatinib mesylate + 10% liquid maltitol + 30% polyethylene glycol + sodium benzoate + acesulfame potassium + citric acid monohydrate + strawberry flavor + water | INBL2059 | Half bottle freezed | Half bottle freezed | Freezed |

Example 10: Stability Comparison Between Test Formulations and Reference Formulation

TABLE 11

Super-accelerated stability study of test formulations and reference formulation

| Composition | 9.56% Imatinib mesylate + 10% liquid maltitol + 30% glycerin + sodium benzoate + acesulfame potassium + citric acid monohydrate + strawberry flavor + water (Test formulation-1) | | 9.56% Imatinib mesylate + 10% liquid maltitol + 20% glycerin + sodium benzoate + acesulfame potassium + citric acid monohydrate + strawberry flavor + water (Test formulation-2) | | 9.56% Imatinib mesylate + 20% Glycerin + 5% Polyvinyl pyrrolidone + 30% Sucrose + sodium citrate dihydrate + citric acid 1 hydrate + Disodium edetate + sucralose + methyl paraben + propyl paraben + sodium metabisulfite (Reference formulation) | |
|---|---|---|---|---|---|---|
| Test parameters Description | Initial Clear yellow solution | 60° C. 7 days Clear yellow solution | Initial Clear yellow solution | 60° C. 7 days Clear yellow solution | Initial Clear yellow solution | 60° C. 7 days Clear yellow solution |
| Related substances | | | | | | |
| RRT-0.00 | — | — | — | — | — | — |
| RRT-0.09 | — | — | — | — | — | 0.03% |
| RRT-0.10 | — | — | — | — | 0.03% | — |
| RRT-0.33 | — | — | — | — | 0.09% | 0.03% |
| RRT-0.48 | 0.08% | 0.09% | 0.08% | 0.09% | 0.08% | 0.09% |
| RRT-0.49 | — | — | — | — | — | — |
| RRT-0.59 | 0.03% | 0.03% | 0.03% | 0.03% | 0.03% | 0.03% |
| RRT-0.60 | — | — | — | — | — | — |
| RRT-0.64 | — | — | — | — | — | — |
| RRT-0.66 | — | — | — | — | — | — |
| RRT-0.67 | — | 0.06% | — | — | — | 0.06% |
| RRT-0.68 | 0.08% | — | 0.09% | 0.07% | 0.06% | — |
| RRT-0.69 | — | — | — | — | — | — |
| RRT-0.70 | — | — | — | — | 0.03% | — |
| RRT-0.84 | — | — | — | — | — | — |
| RRT-0.90 | — | — | — | — | — | — |
| RRT-0.95 | — | — | — | — | — | — |
| RRT-1.20 | 0.12% | 0.13% | 0.12% | 0.13% | 0.12% | 0.12% |
| RRT-1.43 | — | — | — | — | — | — |
| Total impurities | 0.35% | 0.41% | 0.34% | 0.43% | 0.46% | 0.45% |

RRT = Relative retention time

The inventors of the present invention had prepared two formulations as Test Formulation-1 and Test Formulation-2 according to the present invention containing 30% glycerin and 20% glycerin respectively. The inventors have compared these two test formulations with reference formulation prepared according to WO 2014041551. From above table it can be seen that both the test formulations have total impurities less than the reference formulation.

Example 11: Effect of Polyvinyl Pyrrolidone on Liquid Dosage Forms of the Present Invention In order to find out the effect of viscosity regulating agent preferred in the specification of '551 publication (i.e. polyvinyl pyrrolidone) on the liquid dosage forms of the present invention, the inventors of the present invention prepared two formulations, (i) with polyvinyl pyrrolidone, and (ii) without polyvinyl pyrrolidone. These two formulations were tested for its stability after seven days when kept under super-accelerated conditions, i.e. 60° C. The results are summarized in the table below.

| Composition | 9.56% Imatinib mesylate + 10% liquid maltitol + 30% glycerin + sodium benzoate + acesulfame potassium + citric acid monohydrate + strawberry flavor + water | | 9.56% Imatinib mesylate + 10% liquid maltitol + 30% glycerin + 5% polyvinyl pyrrolidone + sodium benzoate + acesulfame potassium + citric acid monohydrate + strawberry flavor + water | |
|---|---|---|---|---|
| Test parameters | | | | |
| | Initial | 60° C. 7 days | Initial | 60° C. 7 days |
| Description | Clear yellow solution | Clear yellow solution | Clear yellow solution | Dark brownish solution |
| Related substances | | | | |
| RRT-0.48 | 0.08% | 0.09% | 0.08% | 0.09% |
| RRT-0.59 | 0.03% | 0.03% | 0.03% | 0.03% |
| RRT-0.67 | 0.08% | 0.06% | 0.08% | 0.06% |

-continued

| | Composition | | | |
|---|---|---|---|---|
| | 9.56% Imatinib mesylate + 10% liquid maltitol + 30% glycerin + sodium benzoate + acesulfame potassium + citric acid monohydrate + strawberry flavor + water | | 9.56% Imatinib mesylate + 10% liquid maltitol + 30% glycerin + 5% polyvinyl pyrrolidone + sodium benzoate + acesulfame potassium + citric acid monohydrate + strawberry flavor + water | |
| | Test parameters | | | |
| | Initial | 60° C. 7 days | Initial | 60° C. 7 days |
| RRT-0.90 | — | — | 0.09% | 0.12% |
| RRT-0.95 | — | — | 0.06% | 0.09% |
| RRT-1.20 | 0.12% | 0.13% | 0.12% | 0.13% |
| RRT-1.43 | — | — | — | — |
| Total impurities | 0.35% | 0.41% | 0.46% | 0.58% |

RRT = Relative retention time

From above data, it can be seen that the appearance of the liquid dosage form without polyvinyl pyrrolidone does not change after one week whereas the appearance of the liquid dosage form with polyvinyl pyrrolidone changes from clear yellow solution to dark brown solution. Further, it can also be seen that the percentage amount and numbers of impurities dramatically increases in the liquid dosage form with polyvinyl pyrrolidone at initial stage and even after one week. Upon looking at the stability study data, the liquid dosage form without polyvinyl pyrrolidone found more stable than liquid dosage form with polyvinyl pyrrolidone.

From the foregoing examples, it is apparent that the liquid dosage forms of Imatinib prepared according to the present invention are suitable for use in the industry.

It should be understood that various changes and modifications to the embodiments described herein will be apparent to those skilled in the art. Such changes and modifications can be made without departing from the spirit and scope of the subject matter of the present invention and without diminishing its intended advantages. It is therefore intended that such changes and modifications be covered within the scope of the present invention.

The invention claimed is:
1. A liquid dosage form consisting of:
about 0.01% to about 25% w/v of imatinib mesylate;
about 25% to about 60% w/v of glycerin;
about 0.01% to about 10% w/v of sodium benzoate;
about 0.01% to about 10% w/v of liquid maltitol;
citric acid;
acesulfame potassium;
strawberry flavor; and
water.

* * * * *

UNITED STATES PATENT AND TRADEMARK OFFICE
CERTIFICATE OF CORRECTION

PATENT NO. : 11,957,681 B2  
APPLICATION NO. : 16/634475  
DATED : April 16, 2024  
INVENTOR(S) : Sandip Mehta et al.

Page 1 of 1

It is certified that error appears in the above-identified patent and that said Letters Patent is hereby corrected as shown below:

On the Title Page

Item (30) please add:  
Foreign Application Priority Data  
Jul. 26, 2017    (IN)     201721026519  
Mar. 21, 2018    (IN)     201823010403

Signed and Sealed this  
Twenty-eighth Day of May, 2024

Katherine Kelly Vidal  
*Director of the United States Patent and Trademark Office*